(12) United States Patent
Voic et al.

(10) Patent No.: US 10,206,704 B2
(45) Date of Patent: Feb. 19, 2019

(54) METHOD FOR ULTRASONIC TISSUE EXCISION WITH TISSUE SELECTIVITY

(71) Applicant: MISONIX, INCORPORATED, Farmingdale, NY (US)

(72) Inventors: Dan Voic, Cedar Grove, NJ (US); Alexander Darian, Brightwaters, NY (US); Christian Ritter, Oakdale, NY (US); Mircea Paraschiv, Nesconset, NY (US)

(73) Assignee: MISONIX, INC, Farmingdale, NY (US)

( * ) Notice: Subject to any disclaimer, the term of this patent is extended or adjusted under 35 U.S.C. 154(b) by 981 days.

(21) Appl. No.: 14/211,586

(22) Filed: Mar. 14, 2014

(65) Prior Publication Data

US 2014/0276849 A1 Sep. 18, 2014

Related U.S. Application Data

(60) Provisional application No. 61/791,723, filed on Mar. 15, 2013.

(51) Int. Cl.
*A61B 17/00* (2006.01)
*A61B 17/32* (2006.01)

(52) U.S. Cl.
CPC ........... *A61B 17/320068* (2013.01); *A61B 2017/320072* (2013.01); *A61B 2217/007* (2013.01)

(58) Field of Classification Search
CPC ........... A61B 17/320068; A61B 17/14; A61B 17/141
USPC ........................................... 606/167
See application file for complete search history.

(56) References Cited

U.S. PATENT DOCUMENTS

| | | | |
|---|---|---|---|
| 6,527,778 B2 * | 3/2003 | Athanasiou | A61B 10/0233 606/80 |
| 2003/0204199 A1 * | 10/2003 | Novak | A61B 17/320068 606/169 |
| 2004/0034340 A1 * | 2/2004 | Biscup | A61B 18/20 606/1 |
| 2006/0264956 A1 * | 11/2006 | Orbay | A61B 17/1615 606/80 |

* cited by examiner

*Primary Examiner* — Si Ming Ku
(74) *Attorney, Agent, or Firm* — R. Neil Sudol; Henry D. Coleman (57) ABSTRACT

A surgical method utilizes a cutting blade having a thickness along a cutting edge of between about 0.0005 inch and about 0.020 inch and preferably between about 0.001 inch and 0.010 inch. The blade is moved in contact with relatively hardly tissues which are disposed adjacent to softer tissues at a surgical site in a patient. The blade is ultrasonically vibrated during the moving of the blade, whereby the hard tissue is cut with a modicum of damage being inflicted on the soft tissue.

20 Claims, 7 Drawing Sheets

METHOD FOR ULTRASONIC TISSUE EXCISION WITH TISSUE SELECTIVITY

CROSS-REFERENCE TO RELATED APPLICATION

This application claims the benefit of U.S. Provisional Patent Application No. 61/791,723 filed Mar. 15, 2013, the entire disclosure of which is hereby incorporated by reference.

BACKGROUND OF THE INVENTION

This invention relates to a surgical method. More particularly, this invention relates to a method for selectively excising tissue during a surgical procedure. This invention also pertains to an ultrasonic surgical blade utilizable in performing the method.

Over the past 30 years, several ultrasonic tools have been invented which can be used to ablate or cut tissue in surgery. Wuchinich et al. in U.S. Pat. No. 4,223,676 and Idemoto et al in U.S. Pat. No. 5,188,102 disclose such devices.

Ultrasonic surgical devices generally fall into two categories. One is a blunt tip hollow probe that vibrates at frequencies between 20 kc and 100 kc, with amplitudes up to 300 microns or more. Such devices ablate tissue by either producing cavitation bubbles which implode and disrupt cells, tissue compression and relaxation stresses (sometimes called the jackhammer effect) or by other forces such as microstreaming of bubbles in the tissue matrix. The effect is that the tissue becomes liquefied and separated. It then becomes emulsified with the irrigant solution. The resulting emulsion is then aspirated from the site. Bulk excision of tissue is possible by applying the energy around and under unwanted tumors to separate it from the surrounding structure. The surgeon can then lift the tissue out using common tools such as forceps.

A second kind of ultrasonic device uses a sharp blade instead of a blunt hollow probe. Here a cutting action takes place. Such a sharp ultrasonic blade is the subject of U.S. Pat. No. 6,379,371. As disclosed therein, the blade shape is semicircular at the distal portion with two straight sides parallel to the longitudinal axis and extending back to the shoulder that contacts the vibrating probe. Male threads are shown which mate with the female threaded socket of the probe (or transducer) to allow tight intimate contact of the probe and blade tip shoulder. When the two are torqued together, they form a single resonant body that will vibrate in sympathy with the transducer and generator combination. The distal end of the blade will vibrate with an amplitude set by the mechanical gain of the probe/tip geometry and the input amplitude provided by the transducer generator combination. This motion provided the cutting action for the tissue in question.

The blade of U.S. Pat. No. 6,379,371 was intended for the cutting or excising of bone or similarly hard tissue in surgical applications. In tests conducted in vitro and in vivo, it was noted that the blade, when sharp, cut both hard and soft tissue with similar ease. In delicate operations, such as sinus lift surgery or craniotomies where the goal is to cut an aperture in the front of the skull to expose sinus tissue or brain but not cut the membrane directly beneath the bony structure, this is very important. It is also important in spinal and brain surgery where bone tissue must be cut with a minimum of damage to underlying soft tissues such as the dura mater. It was noted in early in vitro testing that the blade, as it plunged through the cortex of the bone punctured the membrane or ripped it. After some experience, competent surgeons were able to master the technique, but the learning curve was steep.

A sharp blade such as that of U.S. Pat. No. 6,379,371 has been shown in both in vitro and in vivo testing to be an effective tool for cutting bone, cartilage, soft tissues such as vein, arteries and can even be used to cut skin with minimal secondary trauma. In this kind of blade, ablation is not the primary cause but a shearing or cutting action predominates.

Both the ablating instrument and the cutting or incising instrument have limitations when used as surgical tools. The blunt probe is effective in ablating or excising soft liquid rich tissues such as fat, liver or spleen, but less effective or even non-effective in dry, hard material such as hard cartilage or bone. The blade type devices are effective in the hard material but also are not soft tissue sparing so that collateral tissue damage is incurred, rendering the blade undesirable around nerve clusters or other important structures. Because sharp blades tend to cut everything, tissue selectivity is reduced to nil and no differentiation may be made between hard and soft material.

In certain applications, such as sinus cavity lifts and maxialfacial surgery such as third molar extraction, a tool would be useful which could cut the harder bony material with less trauma while sparing the soft tissues underneath if they were inadvertently touched by the vibrating blade.

OBJECTS OF THE INVENTION

An object of the present invention is to provide a surgical method that selectively excises tissue.

A more specific object of the present invention is to provide a surgical method for cutting harder bony material while minimizing trauma to adjacent soft tissues.

These and other objects of the invention will be apparent to those skilled in the art from the drawings and descriptions hereof. Although each object is attained by at least one embodiment of the invention, no embodiment need necessarily meet every object.

SUMMARY OF THE INVENTION

The present invention is directed principally to a surgical method of using an ultrasonic surgical blade. The preferred surgical blade has a certain range of a critical dimension that permits it to be used in the method.

Figure 1:
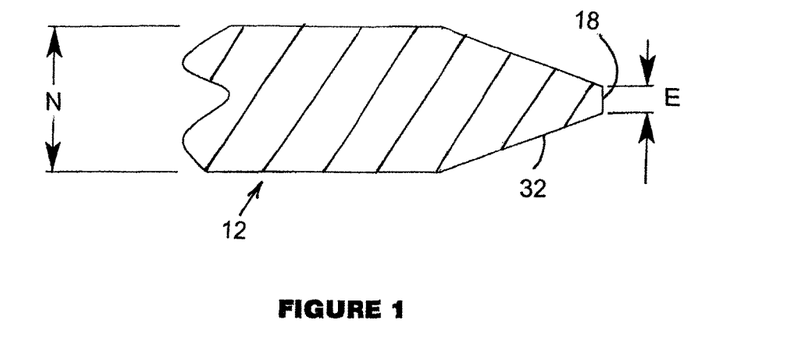
FIG. 1 is a schematic cross-sectional view, on an enlarged scale, of an ultrasonic surgical blade in accordance with the present invention.

The invention was made only upon the observation that the sharper the blade, i.e., the smaller the minor dimension of a vertical trapezoid formed by the included angle of a blade of width N (see FIG. 1), the more likely that cutting of hard tissues resulted in collateral damage, particularly incisions, in surrounding soft tissue. The minor dimension or thickness of the blade at the edge can range from the width of the body of the blade, N, to 0. The degree of sharpness is inversely proportional to the edge thickness.

Dimensionally, it was discovered that blades with an edge thickness between approximately 0.001" and approximately 0.010" inch offered the best compromise between effective, safe cutting of hard tissue such as bone while being sparing of surrounding soft tissue.

As an added benefit, it was serendipitously noted that the blades with a less sharp configuration held their edge longer, i.e., sustained less damage than the sharper blades. It should be noted that the blades did not incur as much damage to the blade surface as the sharper blades, not that the blades started out not sharp and got worse as they were used.

Accordingly, an ultrasonic surgical blade used in a method in accordance with the present invention comprises a generally flat blade having a thickness along a cutting edge of between about 0.0005 inch and about 0.020 inch. More preferably, the cutting edge has a thickness of between about 0.001 inch and 0.010 inch. Most preferably, the cutting edge has a thickness of between about 0.001 inch and 0.003 inch. Generally, the blade has a flat body portion with a body thickness greater than the edge thickness. The blade then includes a beveled or tapered region extending from the body portion to the edge.

A surgical method in accordance with the present invention comprising (a) providing such an ultrasonic surgical blade, (b) inserting the blade into bone tissue without a visual aid to enable visual monitoring of the progress of the blade, (c) during the inserting of said blade, ultrasonically vibrating said blade, the cut formed by said blade being too narrow to allow visual inspection, and (d) terminating the inserting of the blade upon detecting a tactile change indicating contact with soft tissue.

The tactile change naturally occurs in part because the soft tissue is not as resistive to the advance of the ultrasonic instrument. The vibration characteristics of the instrument change upon the tip's encountering of soft tissue.

Pursuant to special features of the ultrasonic surgical blade, the cutting edge is disposed in a single plane and has an arcuate section and a pair of straight sections continuous with the arcuate section at opposite ends thereof. Also, the blade is provided with a shank having an axially extending bore for the conveyance of cooling fluid to the cutting edge, the blade body being provided with an axially extending through-slot communicating at one end with the bore.

A surgical method in accordance with the present invention utilizes a cutting blade having a thickness along a cutting edge of preferably between about 0.0005 inch and about 0.020 inch and more preferably between approximately 0.001 inch and approximately 0.010 inch and most preferably between about 0.001 inch and 0.003 inch. During the performance of the surgical method, the blade is moved in contact with relatively hard tissue that is disposed adjacent to relatively soft tissue at a surgical site in a patient. The cutting edge may be moved at any angle relative to a surface of the hard tissue, from 90° (perpendicular) to 0° (parallel). In the latter case, the blade may move generally along an interface between the relatively hard tissue and the relatively soft tissue. The blade is ultrasonically vibrated during the moving of the blade, whereby the hard tissue is cut and, in the case of an interface incision, separated from the soft tissue, with a modicum of damage being inflicted on the soft tissue.

Pursuant to another feature of the present invention, the vibrating of the blade is initiated prior to a contacting of the surgical site with the blade and is maintained during an initial contact of the blade with the tissues at the surgical site and during the moving of the blade. The blade is moved in a continuous and uninterrupted stroke, for instance, along an interface, the ultrasonic vibrating of the blade being performed continuously and uninterruptedly during the stroke. At the end of the cutting stroke, the ultrasonic vibrating of the blade is terminated and the blade is removed from the surgical site. Irrigation fluid may be introduced to the surgical site during the moving of the blade along the interface.

DETAILED DESCRIPTION

As illustrated in the drawings, a cutting blade 12 for use in ultrasonically assisted surgery includes an integral shank portion 14 having an external screw thread (not shown) for replaceably mounting the blade to a probe. Alternatively, blade 12 may be permanently attached to the probe.

Blade 12 includes a planar blade body 16 having a thickness N. Blade body 16 is provided at an end opposite shank 14 with a blade or cutting edge 18 including a central circularly arcuate section 20 and a pair of linear end sections 22 and 24. Edge 18 is continuous along a full radius of arcuate section 20, as well as along straight sections 22 and 24.

As further illustrated in the drawings, blade 12 also incorporates structure providing a path for coolant from an irrigation pump (not shown) to reach blade edge 18, as well as tissues being cut during a surgical procedure. For conducting irrigant to blade edge 18 and the surgical site, shank portion 14 is formed with an axial passageway or bore 26, which communicates with an axial passageway or bore in the probe.

Passageway or bore 26 terminates in an open longitudinal channel or slot 28 that enables the coolant to spread out and onto the planar body 16 of blade 12. This open channel or slot 28 distributes irrigant all along the sides or lateral surfaces of planar blade body 16 and not in only specific locations, as discussed in U.S. Pat. No. 6,379,371, the disclosure of which is hereby incorporated by reference. At an end of channel or slot 28 opposite passageway or bore 26 is disposed a pair of opposed inclined surfaces 30 (only one shown) which distribute irrigant from the channel or slot towards arcuate blade edge section 20. The fluid traveling down channel or slot 28 will encounter inclined surfaces 30 which exhibit an incident angle that deflects the fluid into the cut (FIG. 10) while minimizing splash back. Surfaces 30 may be planar, convex or concave.

Blade 12 has a thickness E along cutting edge 18 of between about 0.0005 inch and about 0.020 inch, more preferably between about 0.001 inch and 0.010 inch, and most preferably between about 0.001 inch and 0.003 inch. Beveled or tapered surfaces 32 extend from the body portion 16 to edge 18. Cutting edge 18, including sections 20, 22 and 24, is disposed, as is the entire blade body 16, in a single plane.

The use of blade 12 in a surgical procedure is described in detail hereinafter. The procedure described herein is a modification of the procedure described in U.S. Pat. No. 6,379,371.

In use, blade 12 was found to perform best when the following method was employed.

After the patient is prepped for surgery as per standard practices, the ultrasound unit is set up as indicated in U.S. Pat. No. 6,379,371. Upon an activation of the ultrasound unit, blade 12 begins to vibrate and irrigation fluid is introduced simultaneously. Blade edge 18 is then brought into contact with hard tissue at a preselected surgical site. The vibrating blade 12 is moved in a continuous stroke over the incision site to cut or remove tissue to a desired depth. After termination of the stroke, the power to the ultrasound unit is shut off and blade 12 is removed from the surgical site.

The technique discussed above prevents tissue temperature rise to levels that would cause necrosis. If blade 12 is not moved across the surgical site in a wiping or swiping fashion, tissue temperatures quickly increase to over 49 degrees C., which in the human body is at or above the necrosis temperature. By constantly moving the blade, the temperatures rise very little over that of normal body temperatures. Also, this technique provides very good tactile feedback to allow the surgeon to discriminate between the harder tissue and the softer, viable structures.

If surgeon desires and there is enough access, he or she may move blade 12 so that it cuts along an interface between harder and softer tissues, thereby stripping the harder top layer off the soft tissue underneath. Blade 12 has good selectivity between the two layers, so that collateral damage to the soft tissue is minimized.

Preferably, a mixture of saline, lidocaine (or equivalent) and epinephrine (or equivalent) is used as the irrigant. Such a mixture provides moisturization, a slight hemostasis due to the vasocontricting action of the epinephrine, and pain relief from the action of the lidocaine. All of these chemicals have been found to be safe when used for the stated purpose in clinical practice.

Although the surgical method described hereinabove has proven efficacious and safe in adult and pediatric maxialfacial surgery, reconstructive plastic surgery of the face and in various dental procedures, many other surgical procedures may benefit from this invention. Such other surgical procedures include brain and spinal cord surgery where bone tissue must be displaced to afford access to the tissues of the central nervous system. The present invention facilitates such surgery in that the relatively hard bone tissue may be cut with a modicum of damage inflicted on the underlying relatively soft nerve tissues and dura mater. Thus, the present invention is of use in surgery where an incision is to be made perpendicularly to an outer tissue surface or parallel to an exterior surface, e.g., along a hard-tissue/soft-tissue interface.

Ultrasonic bone cutting blade 12 with a blunt tip as disclosed herein is non-abrasive, tissue selective, cuts longitudinally, and can be used blindly, that is, without visualizing the operative tip of the instrument and without significantly damaging underlying soft tissue. The blade cuts a narrow path so that visualization around the blade is not possible. Damage to underlying soft tissues is prevented insofar as the bluntness of the blade and the softness of the tissue cooperate to diffuse the energy before irreparable damage is done. Tactile feedback from the instrument enables the surgeon to withdraw the blade from the patient before the energies delivered to the soft tissue can damage the tissue.

Thus, in using the present surgical blade to cut through bone, one cuts towards the nerve—not away from it. Compared to powered devices like burr and saw, a blunt blade in accordance with the present invention provides better control of the cut and thus higher precision. Third, the blunt blade is tissue selective and provides tactile feedback. One senses when going through the outer cortical into the cancellous and finally touching on the inner cortical layer. Conventional burrs and saws do not do that and cut as aggressively through any bone and soft tissue. Moreover, the surgeon can sketch the kerf as with a fountain pen. No other surgical cutting device offers such a straight path osteotomy. Saws bend and stray, burrs walk sideways, Kerissons leave bite edges, other piezo devices lack in performance to offer a long and deep osteotomy. All other piezo or ultrasonic bone cutting devices use serrations with teeth or abrasive surfaces. A surgical cutting blade as described herein allows full and blind insertion of the entire blade length longitudinally into the bone up to 10/20/30 mm into the bone. The blade base may act like a safety stop for further insertion.

In using the blunt surgical blade of the present invention, one relies on tactile feedback when cutting. One stops ultrasonic cutting when breaching the inner cortical and palpates with the non-active tip in order to feel one's way through. The method may be used in neurosurgical and orthopaedic spine procedures including laminectomies, laminotomies, laminoplasties, facetectomies, carpectomies, and bone graft harvesting from iliac crest.

Figures 2, 3:
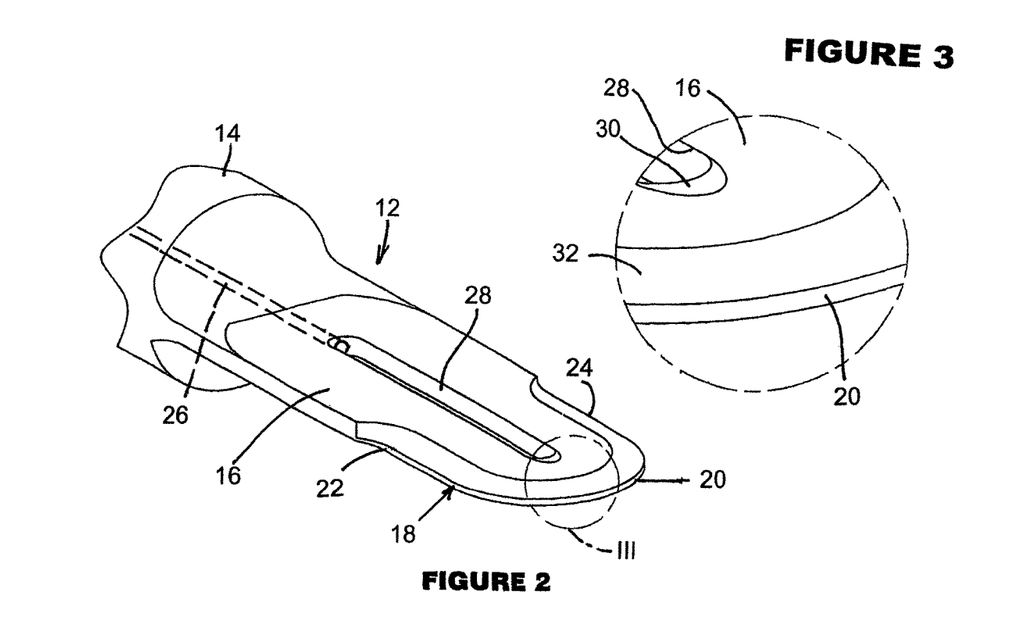
FIG. 2 is a perspective view, also on an enlarged scale, of an ultrasonic surgical blade in accordance with the present invention.
FIG. 3 is a perspective view, on a larger scale, of a portion of the blade encircled by line III in FIG. 2.
Figure 4A:
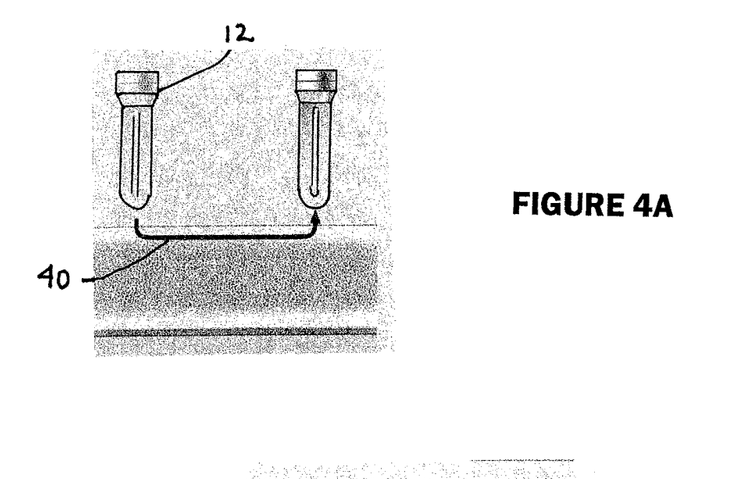
FIGS. 4A-4C are diagrams showing successive steps in an ultrasonic surgical procedure in accordance with the present invention.
Figure 4B:
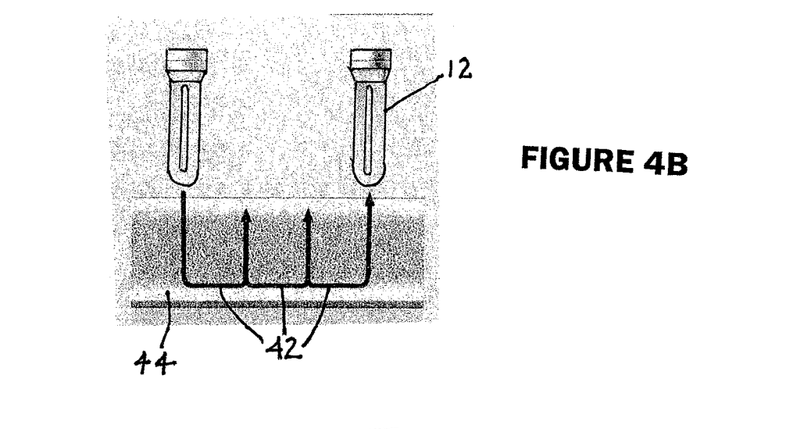
Figure 4C:
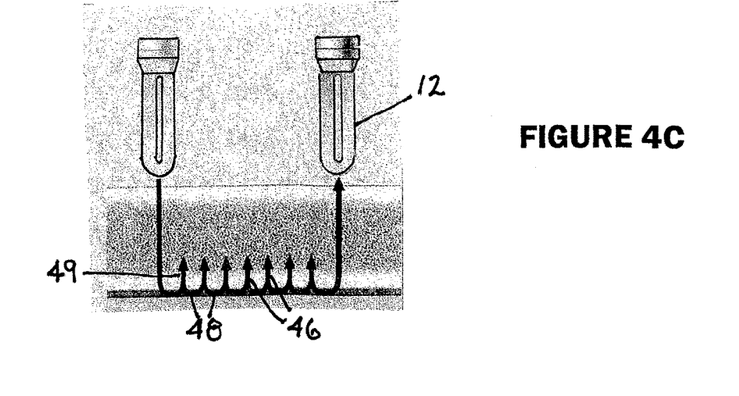

A bone cutting blade 12 as described herein with reference, for example, to FIG. 2 works more efficiently with downward (axial) pressure rather than side-to-side (lateral)

movements. A useful strategy for cutting bicortical bone consists of the following three steps:

1. Using lateral movement 40 with little axial pressure to score the outer cortex of bone to be cut (FIG. 4A).
2. Using axial pressure and liberal lateral sweeps 42 to cut through the cancellous mid-portion 44 of the bone (FIG. 4B).
3. Use a controlled cyclical forward/backward movement 46 with short lateral sweeps 48 to penetrate the inner bone cortex (FIG. 4C). This step primarily involves the use of controlled axial (downward) pressure. Once the surgeon palpates the intended breach of the inner cortex, he withdraws the blade 12 slightly as indicated at 49, moves slightly to one side in a short lateral sweep 48 and repeats the sequence. It is important to note that one generally cannot visualize the underlying soft tissues through the thin trough that is created and must rely on tactile feedback. If unsure of having penetrated the cortex, the surgeon can momentarily stop the ultrasonic action, palpate the inner cortex with the blade 12, and then resume cutting.

In carrying out the above-described surgical technique, one should avoid plunging through the inner cortex of bone in an uncontrolled fashion. As with any other surgical tool, such plunging may cut the dura and result in neural injury. One should not linger over the dura. Once the inner cortex in penetrated, the bone cutting blade 12 (FIG. 2) is promptly withdrawn. Also, one should not use the bone cutting blade 12 when dura is adherent to the inner bone cortex (e.g. re-do laminotomy, ossification of posterior longitudinal ligament, etc.). In these settings, the dura is at risk, since it cannot move away from the blade 12 after the latter penetrates the inner cortex. Furthermore, even if the bone is cut uneventfully, elevating it en bloc from the underlying adherent dura is likely to result in dural laceration.

It is recommended that a prospective user of the bone cutting blade 12 develop a tactile "feel" for the blade by practicing on a cadaver. It is important not only to develop a feel for when the inner cortex is penetrated, but also to familiarize oneself with the amount of axial pressure that is required to cut through bone efficiently. One should palpate with the blade 12 turned off. If unsure of whether the inner bone cortex has been penetrated, it is advisable to momentarily terminate blade vibration and "palpate" the residual bone with blade 12.

It is important to plan an operation. Unlike hand instruments or a power drill, blade 12 removes bone en bloc. It is, therefore, imperative that one plans in advance and defines the boundaries of the bone to be cut. Suggested cutting plans are presented hereinafter for various spine projects.

Blade 12 must be long enough. If the bone to be cut (e.g. a hypertrophic facet) is thicker than the longest available bone cutting blade, the bone will have to be thinned with a rongeur or drill before it can be cut. Bone thickness can be determined from the preoperative imaging studies.

An operation can be divided into pieces. Although it may appear counter-intuitive, it is often more efficient to divide a large bone cutting project (e.g., removing a whole lumber lamina) into two or three smaller pieces. Doing so will improve visualization of the thicker or deeper portions of the bone to be cut and will facilitate elevation of cut bone blocks from the underlying ligaments.

Lumbar Laminotomy

Figure 5A:
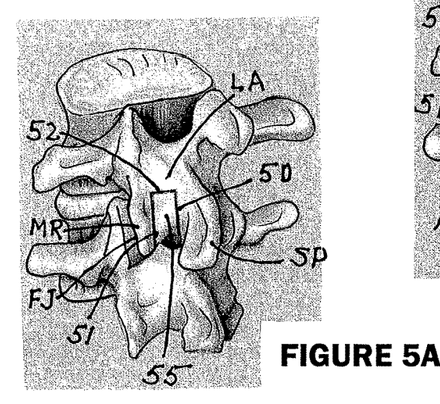
FIGS. 5A-5C are perspective views of a portion of spine, showing successive steps in a spinal surgical procedure in accordance with the present invention.

In a lumbar laminotomy, a minimum of three cuts are required: (1) a sagittal cut 50 along the base of spinous process SP, (2) a sagittal cut 51 along the medial rim MR of the facet joint FJ, and (3) a transverse cut 52 in the lamina LA to connect the previous two cuts (FIG. 5A).

Figure 5B:
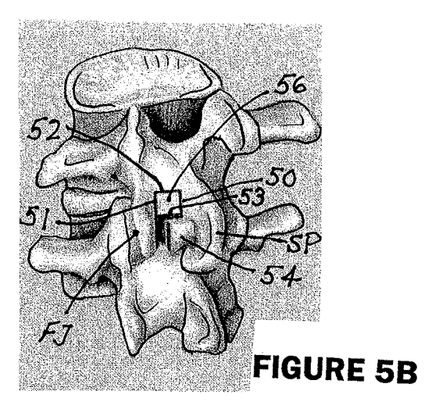

When the exposure has been obtained through a small skin incision, one will find it easier to divide this project into two pieces (FIG. 5B). After making the two sagittal cuts 50 and 51, one may make a transverse cut 53 lower on the lamina LA to remove a lower half 54 (FIG. 5B) of the laminotomy block 55 (FIG. 5A). This provides better exposure of an upper half 56 of the laminotomy block 55, which sits deeper in the wound. The upper block half 56 is mobilized and removed after transverse cut 52 is made, higher on the lamina.

Figure 5C:
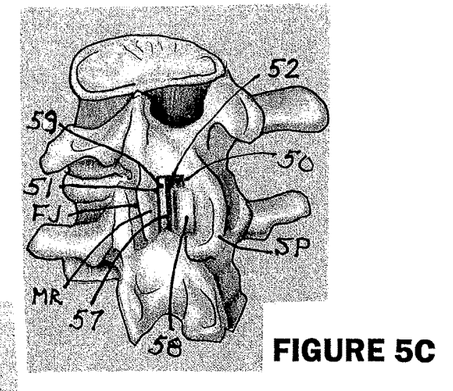

When a hypertrophic facet joint is present, one may arrange the cuts differently, with an additional sagittal cut 57, as depicted in FIG. 5C. First, one makes sagittal cut 50 along the base of spinous process SP, then sagittal cut 57 is made—which is at a more medial location than that of cut 51 in FIG. 5A. Transverse cut 52 is made in the lamina LA to connect cuts 50 and 57. Transverse cut 52 may extend on a side of sagittal cut 57 opposite cut 50. One may then remove a laminotomy block portion 58. Finally, sagittal cut 51 is made along the medial aspect MR of the facet joint FJ and a slice or thin laminotomy block portion 59 is removed. Visualization of ligamentum flavum and dura after the first step aids with the deeper bone cutting that is required in the second step.

Lumbar Laminotomy

Figure 6:
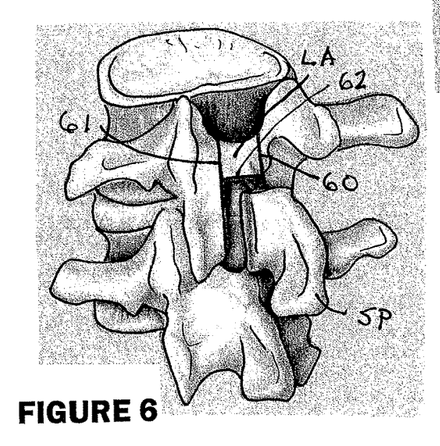
FIG. 6 is a perspective view of a portion of spinal column, showing another spinal surgical procedure in accordance with the present invention.

If one intends to remove only the inferior 'h of the lamina LA, this can be achieved with three cuts: two sagittal cuts 60 and 61 along either side of the spinous process SP, followed by an axial cut 62 across the top of the spinous process (FIG. 6). Of course, it may be easier to remove the spinous process SP with a rongeur prior to making the laminar cuts 60 and 61. If one plans to remove the entire lamina LA, one should consider removing the inferior 'h first. Then remove the superior 'h as a separate block.

Lumbar Facetectomy

Figure 7A:
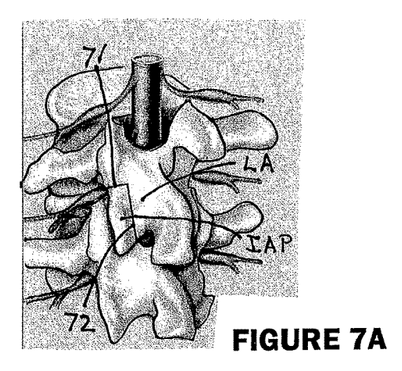
FIGS. 7A and 7B are perspective views of a portion of spinal column, showing successive steps in a further spinal surgical procedure in accordance with the present invention.
Figure 7B:
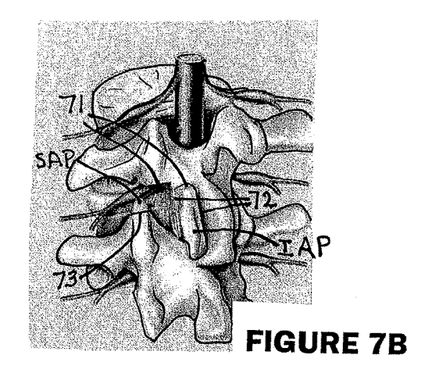

A complete lumbar facetectomy may be required with or without an adjacent laminectomy in certain operations, such as transforaminallumbar interbody fusion. This can be achieved in a rapid and systematic fashion with three cuts. (1) A transverse cut 71 is made along the pars interarticularis. (2) A sagittal cut 72 is made along the lateral aspect of the lamina LA (FIG. 7A). These two cuts allow one to disarticulate and remove the inferior articular process IAP. (3) Once the inferior articular process IAP is removed, the tip of the superior articular process SAP can be amputated with a single cut 73 (FIG. 7B), thus providing a pedicle-to-pedicle exposure of the neural foramen and disc.

Cervical Laminectomy and Laminoplasty

Figure 8A:
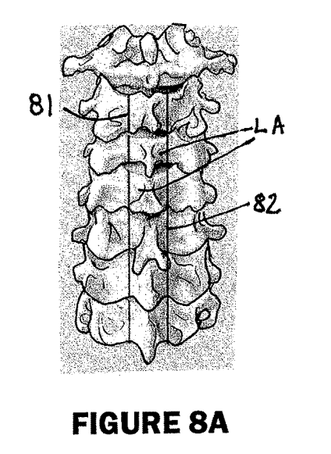
FIGS. 8A and 8B are perspective views of a portion of spinal column, showing successive steps in yet another spinal surgical procedure in accordance with the present invention.
Figure 8B:
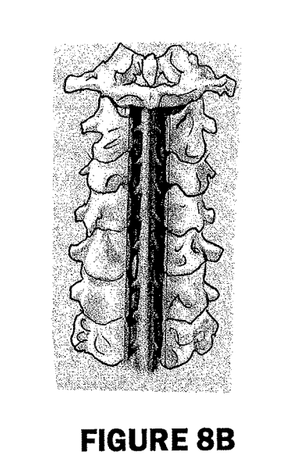

A multilevel cervical laminectomy can be performed expeditiously with bone cutting blade 12 by making two parallel cuts 81 and 82 on either side of multiple laminae LA (FIG. 8). For open-door laminoplasty, one should not penetrate the inner bone cortex on the "hinge" side. The hinge side can be prepared with a drill. Alternatively, one can use bone cutting blade 12 on the hinge side to make two closely-approximated outer-cortical cuts (not shown) which intersect at their depth (with a V-shaped profile), then remove a sliver (not shown) of outer-cortical bone to allow the hinge to open.

Anterior Cervical Corpectomy

Figures 9A, 9B:
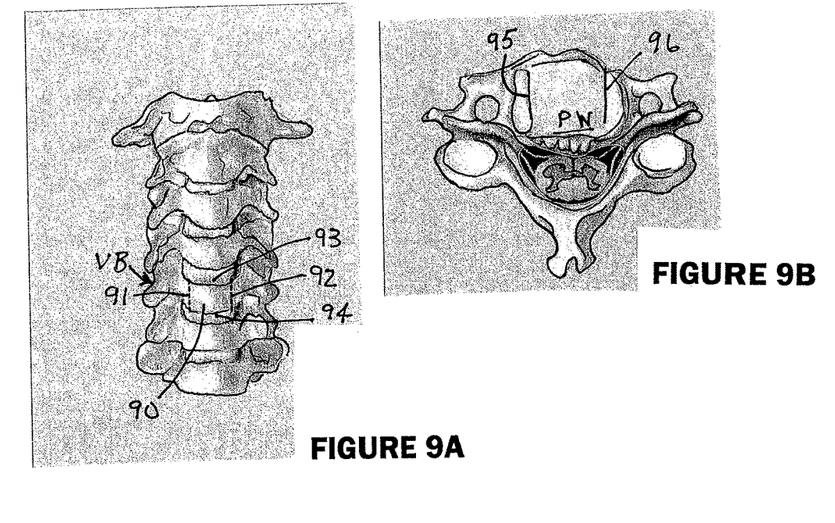
FIG. 9A is an elevational view of a spinal column, showing an initial step in an additional spinal surgical procedure in accordance with the present invention.
FIGS. 9B-9D are transverse cross-sectional views of the spinal column of FIG. 9A, showing additional steps in the surgical procedure of FIG. 9A.
Figure 9C:
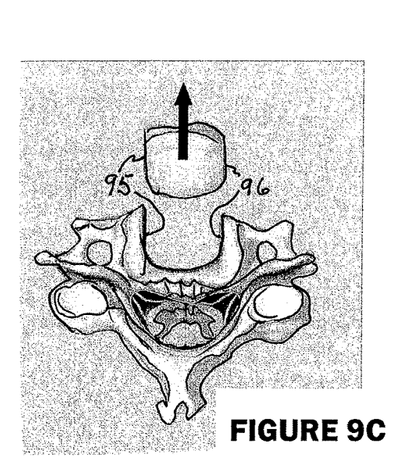
Figure 9D:
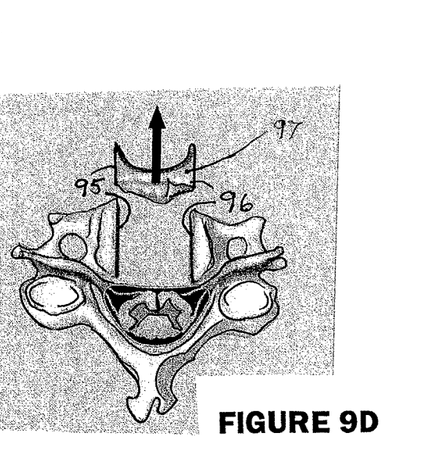

After discectomies have been carried out above and below the level(s) of interest, it is recommended that the anterior portion 90 (FIG. 9C) of the vertebral body VB be removed first. To achieve this, parallel cuts 91 and 92 are made on either side of the vertebral body VB (FIG. 9A), stopping short of the posterior wall and the posterior osteophytes (FIG. 9B). The anterior portion 90 of the vertebral body VB delimited by the two cut planes 91 and 92 and two disc spaces 93 and 94 can be removed with a large rongeur (FIG. 9C). The removal of this bone portion 90 provides for better exposure and greater control during a subsequent use of bone cutting blade 12 to make parallel cuts 95 and 96 through the posterior wall PW. A dissected portion 97 of the posterior wall PW is then carefully elevated and removed (FIG. 9D).

Caution must be exercised to avoid plunging with bone cutting blade 12, particularly in a stenotic canal with cord compression. During elevation of the posterior wall PW, one must avoid rocking one end of the dissected bone portion 97 into the spinal canal SC as the other end is being elevated. Finally, this technique is not suitable for circumstances where the dura may be adherent to the posterior wall PW, as in ossification of posterior longitudinal ligament.

Anterolateral Lumbar or Thoracic Copectomy

This is an advanced ultrasonic bone cutting technique that should be attempted only after one has developed competence and confidence with the use of bone cutting blade 12 in other operations. The technique for removal of a thoracic or lumbar vertebral body through an anterolateral approach is dependent on the pathology for which the operation is being performed. Often tumors and infections will have softened the bone to the point that removal of the mid-portion of the vertebral body does not present a challenge. If necessary, bone cutting blade 12 can be used in combination with rongeurs and drills to facilitate this step. Thorough removal of bone in this step (to get as close as possible to the posterior vertebral body wall) will facilitate the subsequent steps.

Figure 10:
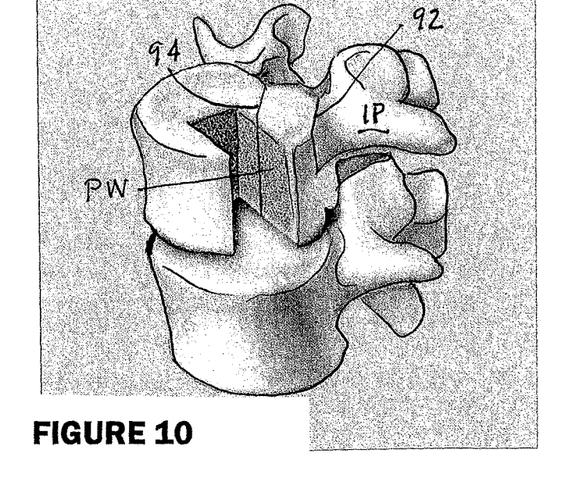
FIG. 10 is a perspective view of a portion of spinal column, showing yet a further spinal surgical procedure in accordance with the present invention.

The main challenge is removal of the posterior vertebral body wall to expose and decompress the spinal canal. After the neural foramen and pedicle are partially exposed and the mid-portion of the body is removed, a cut 92 is made with bone cutting blade 12 at the junction of the ipsilateral pedicle IP and vertebral body toward the spinal canal SC. A second cut 94 is made through the cavity in the vertebral body toward the contralateral side of the spinal canal. The posterior wall PW is then carefully elevated away from the canal and removed (FIG. 10).

Maxillary and Mandibular Osteotomies

Bone cutting blade 12 (FIG. 2) may be used to perform maxillary and mandibular osteotomies. The standard blade has a straight configuration, 20 mm long and 1.0 mm thick. The distal tip has a rounded shape with bevelled surfaces forming blunt forward-cutting edge 20. Central channel 28 ensures the proper distribution of room-temperature irrigant to all cutting surfaces 20, 22, 24 to provide cooling and lubrication, even when the blade 12 is fully engaged in bone. Several modifications may be made to blade 12 to facilitate maxillary and mandibular osteotomies. Blunt serrations along one longitudinal edge 22, 24 allow bone dissection with one lateral side of the blade, while the contralateral side remains smooth for safe maneuvering within the oral cavity. Depth markers may be etched into the blade surface exemplarily at 3, 5, 10, and 15 mm to gauge blade insertion. A soft, protective element made out of silicone may be disposed at the junction with the handpiece to prevent burns to lips or mucosa. The blade length may be extended, for instance, to 30 mm to accommodate anatomical needs in the maxilla and mandible better.

83 patients (40 males and 43 females) who were scheduled to undergo orthognathic surgery were prospectively enrolled in a study. The patients' mean age at the time of surgery was 29 years (range 13-65 years). Patients with a previous history of orthognathic surgery were excluded from the study. The indications for surgery included the presence of dimorphisms in 71 patients and symptoms of sleep apnea in 12 patients. The study included 49 Le Fort I osteotomies, 19 maxillary expansions, 5 mandibular expansions, 102 sagittal split osteotomies, and 8 genioplasties. In addition, 40 hi-maxillary procedures were performed. A 20 mm bone cutting blade 12 was utilized for all osteotomies in patients 1-67, and the 30 mm blade version was used in patients 68-83. The bone cutting blade 12 sold by Misonix, Incorporated under the trademark BoneScalpel™ operates at a nominal, nonmedulated frequency of 22.5 kHz, and the amplitude of vibration ranges from 35 to 300 µm. While amplitude settings of 1-10 are available, a setting of 7 was well suited to the range of bone qualities encountered. Room temperature 0.9% saline solution is delivered through an integrated peristaltic pump that moves fluid through the central hand piece channel to the blade. The irrigant flow rate is adjustable from 15 to 80 ml/min, which corresponds to console settings of 20-100%. Irrigation at setting 100% was chosen to cool the bone and clean the surgical site. All of the surgical procedures were performed by two senior surgeons while the patients were under general anaesthesia with nasal intubation. The third molars had been removed at least 9 months prior to the orthognathic procedure.

A control scan with a 2 mm thickness (GE Brightspeed) was obtained 2 days postoperatively. Examination was made of the ideal bilateral separation between the maxillary tuberosity and the pterygoid plates. The mandible was digitally isolated from the maxilla and skull to observe the design of the split with OSIRIX Software. The operative time was evaluated objectively with OPERA Software. Patients were questioned about the presence or absence of abnormal sensitivity. Outpatient follow-ups were performed at 15 days, 2 months and up to 3 years after each procedure.

Figure 11:
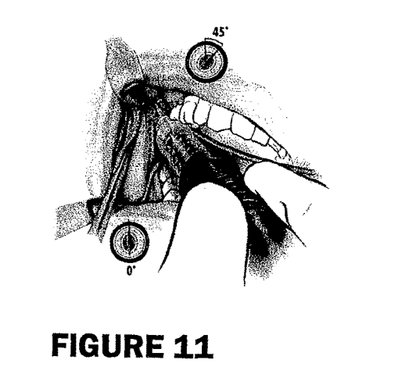
FIG. 11 is a perspective view inside a person's mouth, showing use of an ultrasonic cutting blade (as shown in FIG. 2) to cut the lingual ramus.
Figure 12:
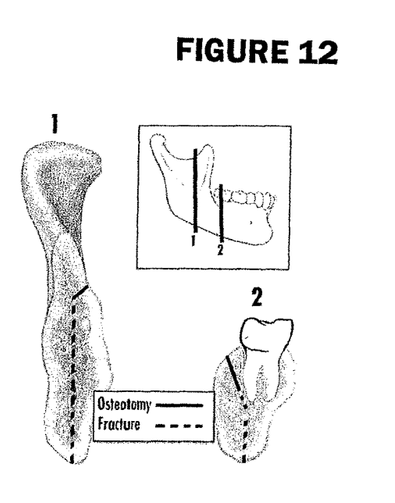
FIG. 12 is a diagram of multiple mouth and jaw bones showing cuts made using an ultrasonic bone cutting blade like that of FIG. 2.
Figures 13, 14, 15:
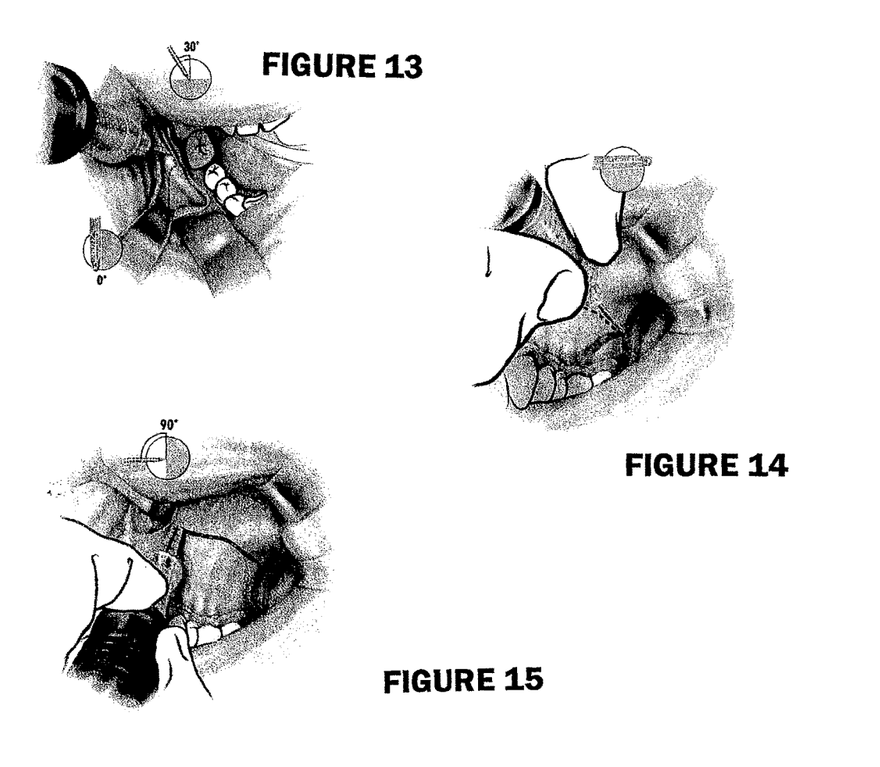
FIG. 13 is a perspective view inside a person's mouth, showing use of an ultrasonic bone cutting blade to cut along an oblique line shown in FIG. 12.
FIG. 14 is a perspective view inside a person's mouth, showing use of an ultrasonic bone cutting blade to cut the tuberosity and the anterior sinus wall.
FIG. 15 is a perspective view inside a person's mouth, showing use of an ultrasonic bone cutting blade to cut the nasal wall.
Figures 16, 17, 18:
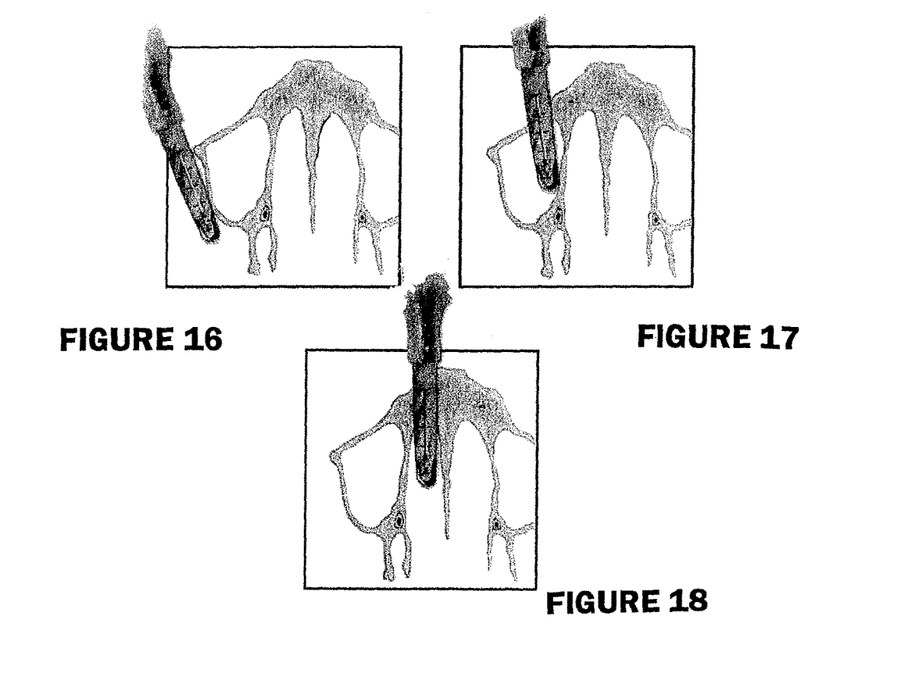
FIG. 16 is a diagram depicting a lateral osteotomy performed by use of an ultrasonic bone cutting blade as shown in FIG. 2.
FIG. 17 is a diagram depicting a medial osteotomy performed by use of an ultrasonic bone cutting blade as shown in FIG. 2.
FIG. 18 is a diagram depicting a septal osteotomy performed by use of an ultrasonic bone cutting blade as shown in FIG. 2.

Fracture lines were classified and compared with those reported in the literature. For the bilateral sagittal split osteotomy (BSSO), the subperiosteal preparations and dissections were performed as usual. The osteotomy was initiated at 45° on the lingual ramus side. The nonactive rigid blade in combination with the serrated profile allowed one to determine the geometry and consistency of the osseous surface (FIGS. 11 and 12). According to the preoperative scans, the blade tip penetrated on the oblique line deeply into the cortical bone at a 30° angle in the direction of the nerve canal without fear of harming the alveolar nerve (FIGS. 12 and 13).

The vertical inferior osteotomy was performed to a level below the basilar region. The split maneuver was easily performed with manual rotation of the osteotomes. For the Le Fort I osteotomies, the subperiosteal preparations and dissections were performed in the usual fashion through sulcular incisions. The straight ultrasonic blade was pulled around the maxillary tuberosity without visual control. The blade was inserted deeper than would be possible with a saw, without fear of causing hemorrhage, to weaken the pterygomaxillary junction and the posterior sinus wall (FIG. 14). The blade was then brought back to the anterior sinus wall to penetrate the lateral nasal wall over the entire length of the septum (FIGS. 15-18). An Obwegeser chisel was applied to all pterygomaxillary sutures, although the disjunction primarily occurred during the use of the ultrasonic device. The maxillary down-fracture was easily obtained with improved control due to an absence of bleeding.

All 183 osteotomies in 83 patients in this study were performed with the use of the BoneScalpel™ ultrasonic osteotome. Its ability to engage bone deeply while maintaining an efficient cutting speed made the use of traditional power instruments, such as saws or burrs, unnecessary. The blade design, with its integrated central channel, was effective in providing irrigant at room temperature to all cutting surfaces, including those that were deep in the bone. Subjectively, the experimenters noted clear reductions in swelling and hematoma formation. In addition, the experimenters observed the complete absence of dental lesions, hemorrhage, facial palsy and perforations of the nasal mucosa. Only 2 cases were observed to have hypoesthesia (1.96%) of the intra-alveolar nerve. The patients were older and treated for symptoms of sleep apnea. An unsatisfactory split occurred only once (0.98%) during the first use of the 30 mm blade due to insufficient power transmission, which was rectified in subsequent cases. This patient had no disturbance of the nerve. Three patients who underwent sagittal split osteotomy developed an infection on the sagittal side (2.94%) due to poor dental hygiene but did not suffer any significant consequences.

Control scans performed after 2 days in patients 53-83 showed different patterns of lingual splitting according to the Plooij et al. classification (Plooij J M, Naphausen M T P, Maal T J J, Xi T, Rangel F A, Swennnen G, et al. 3D evaluation of the lingual fracture line after a bilateral sagittal split osteotomy of the mandible. Int J Oral Maxillofac Surg 2009; 38:1244-9) and different patterns of pterygomaxillary separation according to Robinson and Hendy (Robinson P P, Hendy C W. Pterygoid plate fractures caused by the Le Fort I osteotomy. Br J Oral Maxillofac Surg 1986; 24: 198-202). The results for mandibular splitting were 64.8% using Hunsuck's definition and zero bad splits. For the maxilla, 58.3% showed perfect separation of the pterygomaxillary junction without fracture of the pterygoid plates.

Through the utilization of the ultrasonic bone cutting blade 12, with modifications as pertinent, the most striking observation from 83 patients was a significant reduction in bleeding, which resulted in a clean operative field. Thus, osteotomies of the maxilla, particularly the posterior, were safe and risk free. The placement of retractors can be optimized to avoid stretching of the nerves because of the inherent soft tissue-sparing characteristic of the BoneScalpel™ ultrasonic osteotome. Moreover, this procedure can be performed with four hands.

When performing a BSSO, a preoperative scan precisely displays the lingula and the position of the nerve canal into the ramus.

The straight configuration and the stiffness of the BoneScalpel™ blade serve to increase the accuracy of the osteotomy. Compared with conventional saws and burrs, the ultrasonic blade shows a minimal tendency to deviate from the intended path or walk on bone surfaces. This allows for the placement of the non-active blade in the correct position prior to activating the ultrasound and engaging the bone, which is not possible with the saw. Moreover, the working position is different from the drill or the saw and appears to be more ergonomic, as the blade does not bend during use.

The primary purpose of the serrations added to the lateral side of the blade was to enable the cutting motion along the ramus to remain forward rather than sideways and in accordance with the proposed 45° tilt angle. The 45° angle is critical for initiating the fracture itself, as there is no significant cancellous bone present in this portion of the mandible.

A traditional osteotomy is characterized by a steep, increasing angle from the lingual towards the oblique position. In contrast, the BoneScalpel™ ultrasonic osteotome 12 allows one to continue seamlessly from the lingual ramus towards the oblique at the same 45° angle. Therefore, the cutting force that is introduced at the posterior ramus is better transmitted into the bone, which improves the quality of the lingual osteotomy.

For the horizontal osteotomy, the blade is angled inward towards the nerve canal. The use of the ultrasonic blade is more accurate than the rotary burr or reciprocating saw. The sagittal saw blade is far from rigid, and its lateral flexibility introduces random movements and straying of the saw tip, which make it difficult to maintain the required perpendicular position. Moreover, the risk of slippage with the conventional saw blade is high. In contrast, the new procedure utilizing an ultrasonic osteotome enables the osseous cutting to be more precise and allows for an improved adaption to the anatomy. The tissue-specific cutting resulting from the use of ultrasound technology enables deeper blade insertion for both horizontal and vertical osteotomies, without fear of causing nerve trauma, unlike conventional methods. This is further facilitated by the marker lines on the ultrasonic blade. The propagation of the ultrasonic wave into the cancellous layer facilitates splitting. The thickness of the blade allows for an improved osteotomy line, in accordance with the available width of chisels used to perform the splitting.

As a result of these improvements, the vertical osteotomy is safer, as the position of the nerve is preoperatively ascertained from the imaging scan. With the ultrasonic osteotome, it is possible to slip below the basilar level to reach at least half its width without the risk of damaging the facial nerve. The contralateral vertical osteotomy can easily be achieved by having the surgeon switch sides. In contrast, the reciprocating saw requires caution to maintain a superficial cut and avoid penetrating too deeply into the basilar level, as the inferior alveolar nerve could be located just medial to the cortex.

The kerf is approximately 1.5 mm, which enables osteotomes and a Cryer elevator to be introduced easily above the basal level. This also allows for force uniformity during the split. With this approach, the osteotomies are more accurate and deeper, and the forces required for splitting are much smaller. This also reduces the risk of bad splits because the osteotomies can be well defined according to the individual patient's anatomy and pathology, and this may result in the use of osteotomies in more difficult cases, such as cases of asymmetry, older patients requiring reconstruction or patients with apnea.

The most frequent surgical morbidity associated with BSSO is damage to the inferior alveolar nerve caused by direct mechanical injury, postoperative oedema or compression injury after fixation. Unlike the saw, the straight blade does not require a large dissection for the placement of the retractor, and minimal sub-periosteal elevation decreases this risk. Using the BoneScalpel™ ultrasonic osteotome 12, there was no need to change inserts during use, as the entire procedure was performed utilizing the straight blade.

For LeFort I osteotomies, the blade can be inserted safely without any visual control behind the level of the pterygoid. Closed scissors are currently only used to verify the disjunction with the contact finger at the palate. Adequate pterygoid disjunction was confirmed in the group of 30 patients who were given immediate postoperative CT scans.

Osteotomy of the pillars and nasal septum can be performed using the 30 mm blade without tearing the nasal mucosa. Using the line markers on the 20 mm and 30 mm blades, the experimenters did not risk touching the artery, and can confirm that the osteotomy easily reached the inner sinus walls, which significantly facilitated the maxillary down-fracture. When the down-fracture was initiated, the experimenters were able to complete the osteotomies safely with the BoneScalpel™, especially in the posterior region (i.e. near the emergence of the artery). By entering deeper into the anterior sinus wall, they effectively widened the osteotomy and needed to consider a gap of 1.5 mm for the cephalometric preparation. Compared with the rotary burr or sagitaal saw, the osteotomy line for bone cutting blade 12 is more regular. In posterior maxillary impaction, the osteotomy of the posterior wall is safer with ultrasonic cutting blade 12.

Recent improvements in ultrasonic surgery have proved to be important for advanced orthognathic osteotomies, and the use of ultrasonic instruments, with their associated benefits, is no longer limited to dental surgery. Ultrasonic bone cutting blade 12 with modifications as discussed above allows one to improve the techniques for performing maxillary and mandibular osteotomies in part because of the improved control over bone cuts and the knowledge that the blade would spare soft tissues. This technique resulted in a higher efficiency in the operating room when performing orthognathic osteotomies.

Comparative Advantages

In contrast to bone cutting blade 12 (BoneScalpel™), with a burr one creates a wide trough of 3 mm. As the bone is thinned out it changes color and becomes transparent. It's a visual marker to stop and switch to Kerisson. When using the burr one removes bone, stops to flush with irrigation, remove debris and to check visually for soft tissues and depth.

With a blunt surgical blade as described herein, the trough is only 0.5-1 mm thick and one can not see inside of the trough. The surgeon does not see any bone transparency as the gap is too thin. One uses tactile feedback to feel the different bone layers.

A blunt blade provided with serrations allows one to place the non-active blade in an angle on the mandible. The surgeon feels blindly that the blade is in the right position before engaging the bone and cutting primarily forward with the blunt edge. There is a similar procedure with the shaver tip. One can place the non-active hook blindly under an overhang, feel its correct position and activate the blade.

The lack of wandering/walking/skiving is very important in order to rely on tactile feedback. The blade/tip is put into place and stays were it is. This allows one to cut on curved surfaces.

With a burr, significant effort is necessary to clinically assure the correct position: fluoroscopy with significant, dangerous radiation exposure to the surgeon, repeated intra-operative CT scanning, navigation, robotic guidance (drill). While a blunt surgical blade as described herein can be used with navigation it has the potential to eliminate many of the imaging procedures during surgery.

A blunt surgical blade as described herein allows one to cut towards the nerve. Examples are laminectomy, laminotomy, laminoplasty. One can cut deeper into the maxillary space without fear of damaging nerves and blood vessels, he does that blindly), any type of undercutting, e.g. for harvesting half-thickness bone grafts from the parietal, undercutting bone blocks in hyperplasia, undercutting the contralateral facet from an ipsilateral entry.

The ability to work blindly and precisely is of tremendous value and allows one to alter/adjust surgical techniques. Deeper entry into the pterygomaxillary space improves the Down fracture. Placement of the serrated edge (in the case that the blunt blade is provided with a blunt edge serration) on the mandible improves the sagittal split theoretically. Any form of undercutting becomes easier as it is less worrisome. The hemostatic effect is equally important here as it reduces worries as well.

The smaller kerf is theoretically beneficial for osteogenesis. In placing an autologous cranial craft it is important to place the graft edge to edge at least on one side to stimulate bone growth. The smaller the gap the more contact surface there is.

For cervical laminectomies one leaves two cuts bilaterally of 0.5 mm each, with the burr 3 mm. This results in a bone loss of 1 mm for a blunt blade as described herein versus 6 mm with a burr. It is notable that Mectron has a 0.3 mm saw.

A blunt surgical blade as described herein allows certain orthognathic or even spine procedures on an outpatient basis due to the added safety.

The tissue sparing relies on a tissue's elasticity. Tissues with higher collagen content are less elastic. Boundaries or stretching of nerves can reduce elastic behavior. This is very important for the ability to work blindly.

Tissue sparing does not work with abrasive surfaces like shavers. Also, spine surgeons are initially afraid of the serrations.

The blade body of the present invention is designed to be fully inserted into the bone. Examples are the irrigant film over the entire blade, the safety stop at blade base, the depth markers on the serrated blade. Non-serrated blades may be provided with visual indicators as well for gauging insertion depth. The irrigation channel represents a defined start and end point and even its middle length point can be seen as helpful for gauging depth.

Accordingly, it is to be understood that the drawings and descriptions herein are proffered by way of example to facilitate comprehension of the invention and should not be construed to limit the scope thereof.

What is claimed is:

1. A surgical method comprising:
   providing an ultrasonic surgical instrument comprising a blade having a thickness along a cutting edge of between about 0.0005 inch and about 0.020 inch;
   manually inserting said blade through an outer cortex and cancellous tissue of a bone of a patient;
   manually further inserting said blade into an inner cortex of the patient's bone;
   during the further inserting of said blade, ultrasonically vibrating said blade, said blade preventing a surgeon from seeing at least a distal-most portion of said cutting edge during the further inserting of said blade, where the distal-most portion of said cutting edge is located inside the patient; and
   manually terminating the further inserting of the blade upon detecting via tactile sensation on a part of the surgeon a reduction in resistance to advance of said blade indicating penetration of a distal tip of said blade through a distal or far side of said inner cortex.

2. The method defined in claim 1 wherein said thickness is an edge thickness, said blade having a flat body portion with a body thickness greater than said edge thickness, said blade including a beveled or tapered region extending from said body portion to said edge.

3. The method defined in claim 2 wherein said cutting edge is disposed in a single plane and has an arcuate section.

4. The method defined in claim 3 wherein said cutting edge includes a pair of straight sections continuous with said arcuate section at opposite ends thereof.

5. The method defined in claim 4 wherein said blade is provided with a shank having an axially extending bore for the conveyance of cooling fluid to said cutting edge, said blade being provided with an axially extending through-slot communicating at one end with said bore.

6. The method defined in claim 1 wherein the thickness of said cutting edge is between about 0.001 inch and about 0.010 inch.

7. The method defined in claim 6 wherein the thickness of said cutting edge is between about 0.001 inch and about 0.003 inch.

8. A surgical method comprising:
providing a cutting blade having a thickness along a cutting edge of between about 0.0005 inch and about 0.020 inch;
manually inserting said blade into relatively hard tissue located adjacent to relatively soft tissue at a surgical site in a patient, so that said cutting edge cuts through said hard tissue and leaves said soft tissue substantially intact and undamaged;
ultrasonically vibrating said blade during the inserting of said blade;
forming a cut in the patient by the inserting and ultrasonic vibrating of said blade, the blade preventing a surgeon from seeing at least a distal-most portion of said cutting edge during the inserting of said blade, where the distal-most portion of said cutting edge is located inside the patient; and
manually terminating the inserting of the blade upon detecting via tactile sensation on a part of the surgeon a reduction in resistance to advance of said blade indicating penetration of a distal tip of the blade through a distal or far side of said hard tissue.

9. The method defined in claim 8 wherein the vibrating of said blade is initiated prior to a contacting of said hard tissue with said blade and is maintained during the inserting of said blade through said hard tissue.

10. The method defined in claim 8, further comprising introducing irrigation fluid to said surgical site during the inserting of said blade into the hard tissue.

11. The method defined in claim 8 wherein said blade is moved in a continuous and uninterrupted stroke during the inserting of said blade, the ultrasonic vibrating of said blade being performed continuously and uninterruptedly during said stroke.

12. The method defined in claim 8 wherein the thickness of said cutting edge is between about 0.001 inch and about 0.010 inch.

13. The method defined in claim 8 wherein said hard tissue is tissue of a bone, further comprising, prior to the inserting of said blade, manipulating said blade to score an outer cortex of said bone, further comprising:
applying an axial pressure and a lateral sweeping force to said blade to cut through a cancellous mid-portion of said bone; and
thereafter imparting to said blade a controlled back-and-forth cyclical axial movement with a plurality of lateral sweeps.

14. The method defined in claim 13 wherein the imparting to said blade of a controlled back-and-forth axial movement includes:
pressing the blade multiple times axially into said bone and each of said multiple times terminating the inserting of the blade upon tactilely detecting a reduction in resistance to blade advance indicating penetration of a distal tip of the blade through a distal or far side of said hard tissue;
withdrawing said blade axially; and
moving said blade laterally inside a cut made by the applying of axial pressure and the lateral sweeping force to said blade.

15. The method defined in claim 14, further comprising momentarily interrupting the ultrasonic vibrating of said blade, palpating an inner cortex of said bone with said blade, and subsequently resuming cutting.

16. The method defined in claim 1, further comprising, prior to the inserting of said blade through said outer cortex and said cancellous tissue, manipulating said blade to score said outer cortex, the inserting of said blade through said outer cortex and said cancellous tissue including:
applying an axial pressure and a lateral sweeping force to said blade to cut through a cancellous mid-portion of said bone tissue; and
thereafter imparting to said blade a controlled back-and-forth cyclical axial movement with a plurality of lateral sweeps.

17. The method defined in claim 16 wherein the imparting to said blade of a controlled back-and-forth axial movement includes:
pressing the blade multiple times axially into said bone and each of said multiple times terminating the inserting of the blade upon tactilely detecting a change indicating penetration of a distal tip of the blade through a distal or far side of said hard tissue;
withdrawing said blade axially; and
moving said blade laterally inside a cut made by the applying of axial pressure and the lateral sweeping force to said blade.

18. The method defined in claim 14, further comprising momentarily interrupting the ultrasonic vibrating of said blade, palpating an inner cortex of said bone tissue with said blade, and subsequently resuming cutting.

19. The method defined in claim 1, further comprising continuing the ultrasonic vibrating of said blade during and after the terminating of the inserting of said blade.

20. The method defined in claim 8, further comprising continuing the ultrasonic vibrating of said blade during and after the terminating of the inserting of said blade.

* * * * *